(12) United States Patent
Breulles et al.

(10) Patent No.: US 11,000,523 B2
(45) Date of Patent: May 11, 2021

(54) CERITINIB FORMULATION

(71) Applicant: Novartis AG, Basel (CH)

(72) Inventors: Sebastien Breulles, Nevers (FR); Simon Ensslin, Rheinfelden (DE)

( * ) Notice: Subject to any disclaimer, the term of this patent is extended or adjusted under 35 U.S.C. 154(b) by 0 days.

(21) Appl. No.: 16/571,229

(22) Filed: Sep. 16, 2019

(65) Prior Publication Data

US 2020/0009141 A1    Jan. 9, 2020

Related U.S. Application Data

(63) Continuation of application No. 16/142,263, filed on Sep. 26, 2018, now abandoned, which is a continuation of application No. 15/313,367, filed as application No. PCT/IB2015/053966 on May 27, 2015, now abandoned.

(60) Provisional application No. 62/004,359, filed on May 29, 2014.

(51) Int. Cl.
   *A61K 31/506*       (2006.01)
   *A61K 9/20*         (2006.01)
   *A61K 9/16*         (2006.01)

(52) U.S. Cl.
CPC .......... *A61K 31/506* (2013.01); *A61K 9/1617* (2013.01); *A61K 9/1635* (2013.01); *A61K 9/2013* (2013.01); *A61K 9/2027* (2013.01); *A61K 9/2054* (2013.01); *A61K 9/2059* (2013.01); *A61K 9/2063* (2013.01); *A61K 9/2077* (2013.01); *A61K 9/2095* (2013.01)

(58) Field of Classification Search
CPC .. A61K 31/506; A61K 9/2095; A61K 9/2054; A61K 9/2059; A61K 9/2077; A61K 9/2027
See application file for complete search history.

(56) References Cited

U.S. PATENT DOCUMENTS 3,632,778 A * 1/1972 Sheth .................. A61K 9/2004
                                                                        514/567

FOREIGN PATENT DOCUMENTS

| WO | 20080073687 A1 | | 6/2008 |
|---|---|---|---|
| WO | WO2008/073687 | * | 6/2008 |
| WO | WO2008/073687 A2 | | 6/2008 |
| WO | 2009/100886 | | 8/2009 |
| WO | 2011/142478 | | 11/2011 |

OTHER PUBLICATIONS

Goodman and Gilman's in Goodman and Gilman's The Pharmacological Basis of Therapeutics, Tenth Edition (2001), McGraw Hill, Chapter I, pp. 3-29) (Year: 2001).*
Wilkinson, "Pharmacokinetics the dynamics of drug absorption, distribution, and elimination", Goodman & Gilman's The Pharmacological Basis of Therapeutics, 10th edition (2001), McGraw Hill, ch1, pp. 3-29.
Devi, N. Anjali et al., IRJP 2012, 3(9), 185-193.
Journal of Chemical and Pharmaceutical Research, 2013, 5(11): 617-625.
Journal of Medicinal Chemistry, (Jul. 25, 2013), vol. 56, No. 14, doi:10.1021/jm400402q, ISSN 0022-2623, pp. 5675-5690, XPO55145299.
Shaw et al., Ceritinib in ALK-Rearranged Non-Small-Cell Lung Cancer. New England Journal of Medicine, 2014, 370:1189-1197.
Friboulet et al, The ALK Inhibitor Ceritinib Overcomes Crizotinib Resistance in Non-Small Cell Lung Cancer, Cancer Discovery, Jun. 2014.
Thomas H. Marsilje et al:, "Synthesis, Structure-Activity Relationships, and in Vivo Efficacy of the Novel Potent and Selective Anaplastic Lymphoma Kinase (ALK) Inhibitor 5-Chloro- N 2-(2-isopropoxy-5-methyl-4-(piperidin-4-yl) phenyl)- N 4-(2-(isopropylsulfonyl)phenyl) pyrimidine-2,4-diamine (LDK378) Currently in Phase 1 and Pha", Journal of Medicinal Chemistry, vol. 56, No. 14, Jul. 25, 2013.

* cited by examiner

*Primary Examiner* — Dennis Heyer
(74) *Attorney, Agent, or Firm* — Jennifer Chapman (57) ABSTRACT

The present disclosure relates to a new pharmaceutical composition comprising Ceritinib. Particularly it is directed to the tablet that is prepared by wet granulation, wherein povidone is used as a binder. Further feature of the composition is that the drug and the binder form the inner phase, whereas all other excipients are added in a powder form as an outer phase. This way, the sticking of the composition is prevented and sufficient tablet hardness can be reached.

4 Claims, 3 Drawing Sheets

CERITINIB FORMULATION

FIELD OF THE DISCLOSURE

The present disclosure relates to a new pharmaceutical composition comprising Ceritinib. It further relates to a tablet comprising Ceritinib and a process of preparing said tablet. In addition, the disclosure also related to a use of the pharmaceutical composition or the tablet.

BACKGROUND OF THE INVENTION

WO2008/073687 A1 disclosed ceritinib (also named LDK378) as compound 66 in Example 7. Chemical formula of ceritinib is 5-chloro-$N^2$-(2-isopropoxy-5-methyl-4-(piperidin-4-yl)phenyl)-$N^4$-[2-(propane-2-sulfonyl)-phenyl]-pyrimidine-2,4-diamine.

Ceritinib is an anaplastic lymphoma kinase (ALK) inhibitor. ALK is a member of the insulin receptor superfamily of receptor tyrosine kinases. Genetic alterations of ALK have been implicated in oncogenesis in hematopoietic and non-hematopoietic tumours. The gene has been found to be rearranged, mutated, or amplified in a series of tumours, including non-small cell lung cancer. Ceritinib has been approved by the US FDA as Zykadia® for the treatment of patients with anaplastic lymphoma kinase (ALK)-positive metastatic non-small cell lung cancer (NSCLC) who have progressed on or are intolerant to crizotinib. The approved dosage is a daily dose of 750 mg administered orally, with possible dose reduction in 150 mg increment(s) to 600 mg and 450 mg as needed. The minimum treatment dose is 300 mg. The approved dosage form is a capsule of size 00 containing a 150 mg dose of ceritinib.

SUMMARY OF THE INVENTION

Ceritinib is a difficult compound to formulate. In water, it exhibits solubility of only 0.02 mg/mL (at 25° C.), and together with its low permeability according to the Biopharmaceutics Classification System qualifies for a class IV compound. In addition, physical characteristics of Ceritinib cause sticking and picking during tableting or encapsulation of the drug and make it poorly compressible. Furthermore, the drug is administered at a high dose of 750 mg, which would require a patient to take daily up to 5 units of 150 mg. If the dose is to be increased in a respective dosage form, the increase in drug load generally negatively affects the compressibility of a tablet. Ceritinib's sticky nature causes a high drug load to further negatively influence the manufacturing of tablets due to enhanced sticking/picking.

Surprisingly it was found that a high drug load of more than 40 weight percent, preferably more than 45 wt %, more preferably more than 50 wt %, particularly 60 wt % of Ceritinib in a tablet can be achieved by using a specifically adapted wet granulation process, whereby solely the pharmaceutical active ingredient ceritinib is granulated with a binder. Said wet granulation process also leads to high compressibility and much reduced or even no sticking and picking during manufacturing. The latter can be further improved by adding the right amount of a lubricant, such as for example magnesium stearate. The tablet obtained by employing the disclosed process exhibits suitable hardness and reduced friability. Also of importance is the high drug load of pharmaceutical composition that can be reached. For example, the table can comprise for example 70% by weight of the drug substance. The tablet can be thus of an acceptable size that is more convenient for patients to swallow, even if containing doses up to 375 mg or more. Compared to the capsule, the in vitro dissolution profiles predict that the tablet can also behave in vivo comparably to capsule. The compliance of taking the new formulation is expected to be much improved compared to the one of a capsule given the high daily dose that needs to be administered and inconvenient size of a capsule.

Therefore, one aspect of the present disclosure is a pharmaceutical composition comprising more than 40 and up to 70 weight percent of Ceritinib based on the total weight of the pharmaceutical composition. Further the disclosure provides a tablet comprising Ceritinib obtainable by preparing granules comprising Ceritinib and a binder by wet granulation, mixing the granules with at least one pharmaceutical excipient to obtain a mixture, and compressing the mixture in the tablet.

The pharmaceutical composition and the tablet according to the present disclosure can be used as a medicine. Another aspect of the disclosure is a process of preparing a tablet comprising Ceritinib, wherein the process comprises wet granulation of Ceritinib and a binder, and a compression step.

The aspects, advantageous features and preferred embodiments of the present invention summarized in the following items, respectively alone or in combination, further contribute to solving the object of the invention:

1. A pharmaceutical composition comprising more than 40 and up to 70 weight percent of Ceritinib based on the total weight of the pharmaceutical composition.
2. The pharmaceutical composition according to item 1 comprising at least 45 and up to 70 weight percent of Ceritinib based on the total weight of the pharmaceutical composition.
3. The pharmaceutical composition according to item 1 comprising at least 50 and up to 70 weight percent of Ceritinib based on the total weight of the pharmaceutical composition.
4. The pharmaceutical composition according to item 1 comprising at least 55 and up to 65 weight percent of Ceritinib based on the total weight of the pharmaceutical composition.
5. The pharmaceutical composition according to item 1 comprising 60 weight percent of Ceritinib based on the total weight of the pharmaceutical composition.
6. The pharmaceutical composition according to any one of items 1 to 5, comprising a granule comprising Ceritinib and a binder, wherein the granule is obtainable by wet granulation.
7. The pharmaceutical composition according to item 6, wherein the granule consists of or substantially consists of Ceritinib and the binder.
8. The pharmaceutical composition according to item 6 or 7, wherein the binder is selected from the group consisting of starch, Hypromellose (Hydroxypropylmethyl cellulose), Hydroxypropyl cellulose, Hydroxy ethyl cellulose, Povidone (Polyvinylpyrrolidone), Copovidone (copolyvidone), Gelatine and Polymethacrylate.
9. The pharmaceutical composition according to any one of items 6 to 8, wherein the binder is povidone (polyvinilpyrrolidone).
10. The pharmaceutical composition according to any one of items 1 to 9, further comprising another pharmaceutical excipient.
11. The pharmaceutical composition according to item 10, wherein the pharmaceutical excipient is in a powder form.

12. The pharmaceutical composition according to item 10, wherein the pharmaceutical excipient is in a dry powder form.
13. The pharmaceutical composition according to any one of items 10 or 12, wherein the pharmaceutical excipient is a binder.
14. The pharmaceutical composition according to item 13, wherein the binder is selected from the group of starch, Hypromellose (Hydroxypropylmethyl cellulose), Hydroxypropyl cellulose, Hydroxy ethyl cellulose, Povidone (Polyvinylpyrrolidone), Copovidone (copolyvidone), Gelatine and Polymethacrylate.
15. The pharmaceutical composition according to item 13 or 14, wherein the binder is Hydroxypropyl cellulose low substituted.
16. The pharmaceutical composition according to item 1 to 15, further comprising a lubricant.
17. The pharmaceutical composition according to any one of items 1 to 16, wherein the composition further comprises a filler, disintegrant, glidant, and/or lubricant, or mixture thereof.
18. The pharmaceutical composition according to item 17, further comprising magnesium stearate.
19. The pharmaceutical composition according to item 16 or 17, wherein the lubricant is magnesium stearate.
20. The pharmaceutical composition according to item 18 or 19 comprising at least 0.5 and up to 3 weight percent of magnesium stearate, preferably at least 1 and up to 2 weight percent of magnesium stearate, at least 1.3 and up to 1.7 weight percent of magnesium stearate, particularly 1.5 weight percent of magnesium stearate based on the total weight of the pharmaceutical composition.
21. The pharmaceutical composition according to any one of items 1 to 20 in a form of a tablet or capsule.
22. The pharmaceutical composition according to any one of items 1 to 20 in a form of a tablet.
23. The pharmaceutical composition according to item 22, wherein the tablet has hardness of at least 45 N, preferably at least 50 N, between 50 and 82 N, preferably between 58 and 72 N, most preferably between 64 and 71N, when the tablet contains 150 mg or more and below 300 mg of ceritinib, or has a hardness of at least 100 N, preferably at least 150 N, when the tablet contains 300 mg or more of ceritinib.
24. The pharmaceutical composition according to item 22 or 23, wherein the tablet is obtainable by wet granulation followed by compression.
25. The pharmaceutical composition according to an one of items 22 to 24, wherein the tablet is obtainable by compressing a granule comprising Ceritinib and a binder with at least one pharmaceutical excipient, wherein the granule is obtainable by wet granulation.
26. A tablet comprising Ceritinib obtainable by
   (i) Preparing granules comprising Ceritinib and a binder by wet granulation,
   (ii) mixing the granules with at least one other pharmaceutical excipient to obtain a mixture, and
   (iii) compressing the mixture to obtain the tablet.
27. The tablet according to item 26, wherein the at least one other pharmaceutical excipient is magnesium stearate.
28. The tablet according to item 27, wherein at least 0.5 and up to 3 weight percent of magnesium stearate, preferably at least 1 and up to 2 weight percent of magnesium stearate, at least 1.3 and up to 1.7 weight percent of magnesium stearate, particularly 1.5 weight percent of magnesium stearate based on the total weight of the pharmaceutical composition.
29. The tablet comprising Ceritinib according to any one of items 26 to 28, wherein at least one other pharmaceutical excipient is mixed in dry powder form.
30. The tablet comprising Ceritinib according to any one of items 26 to 29, wherein the binder is selected from the group consisting of starch, Hypromellose (Hydroxypropylmethyl cellulose), Hydroxypropyl cellulose, Hydroxy ethyl cellulose, Polyvinylpyrrolidone, Copovidone (copolyvidone), Gelatine and Polymethacrylate.
31. The tablet comprising Ceritinib according to any one of items 26 to 29, wherein the binder is polyvinylpyrrolidone.
32. The tablet comprising Ceritinib according to any one of items 26 to 31, wherein the tablet comprises at least 40 and up to 70 weight percent of Ceritinib, preferably at least 45 and up to 70 weight percent, more preferably at least 50 and up to 70 weight percent, yet more preferably at least 55 and up to 65 weight percent, particularly 60 weight percent of Ceritinib based on the total weight of an uncoated tablet.
33. The tablet comprising Ceritinib according to any one of items 26 to 32, wherein at least one other pharmaceutical excipient is added in a powder form.
34. The tablet comprising Ceritinib according to any one of items 26 to 33, wherein the at least one other pharmaceutical excipient is a binder.
35. The tablet comprising Ceritinib according to item 34, wherein the binder is selected from the group of starch, Hypromellose (Hydroxypropylmethyl cellulose), Hydroxypropyl cellulose, Hydroxy ethyl cellulose, Polyvinylpyrrolidone, Copovidone (copolyvidone), Gelatine and Polymethacrylate.
36. The tablet comprising Ceritinib according to item 34 or 35, wherein the binder is Hydroxypropyl cellulose low substituted.
37. The tablet comprising Ceritinib according to any one of items 26 to 36, wherein the tablet further comprises a filler, disintegrant, glidant, and/or lubricant, or mixture thereof.
38. The tablet comprising Ceritinib according to any one of items 26 to 37, wherein the tablet has hardness of at least 45 N, preferably at least 50 N, between 50 and 82 N, preferably between 58 and 72 N, most preferably between 64 and 71N, when the tablet contains 150 mg or more and below 300 mg of ceritinib, or has a hardness of at least 100 N, preferably at least 150 N, when the tablet contains 300 mg or more of ceritinib.
39. The pharmaceutical composition according to any one of items 1 to 25, or the tablet according to any one of items 26 to 38, wherein a Ceritinib dose is 150 mg.
40. The pharmaceutical composition according to any one of items 1 to 25, or the tablet according to any one of items 26 to 38, wherein a Ceritinib dose is at least 150 and up to 750 mg, preferably a Ceritinib dose is at least 150 and up to 375 mg, more preferably is at least 300 mg and up to 375 mg, particularly a Ceritinib dose is 300 mg.
41. The pharmaceutical composition according to any one of items 1 to 25, or the tablet according to any one of items 26 to 38, wherein the Ceritinib dose is 375 mg.
42. A granule comprising, consisting of or substantially consisting of Ceritinib and a binder, wherein the granule is obtainable by wet granulation.
43. A process of preparing a tablet comprising Ceritinib, wherein the process comprises wet granulation of Ceritinib and a binder, and a compression step.
44. The process for preparing a tablet comprising Ceritinib according to item 43, wherein the binder is selected from the group consisting of starch, Hypromellose (Hydroxypropylmethyl cellulose), Hydroxypropyl cellulose, Hydroxy ethyl cellulose, Polyvinylpyrrolidone, Copovidone (copolyvidone), Gelatine and Polymethacrylate.

45. The process for preparing a tablet comprising Ceritinib according to item 43 or 44, wherein the binder is Polyvinylpyrrolidone.

46. A process for preparing a granule comprising, consisting of or substantially consisting of Ceritinib and a binder, wherein the process comprises the steps of mixing Ceritinib and the binder and wet granulation to obtain the granule.

47. A process of preparing a tablet comprising Ceritinib according to any one of items 43 to 46, where the process comprises the steps:
    a) Preparing granules comprising Ceritinib and a binder by wet granulation,
    b) mixing the granules with at least one other pharmaceutical excipient to obtain a mixture, and
    c) compressing the mixture to obtain the tablet.

48. The process for preparing a tablet comprising Ceritinib according to any one of items 43 to 47, further comprising the step of calibrating the granule size.

49. The process for preparing a tablet comprising Ceritinib according to any one of items 43 to 48, further comprising depositing a lubricant on the surfaces of a pressing tool, particularly tableting machine punches.

50. The process for preparing a tablet comprising Ceritinib according to any one of items 43 to 49, further comprising coating a tablet.

51. The process for preparing a tablet comprising Ceritinib according to any one of items 43 to 50, wherein mixing in step b) is dry mixing.

52. The process for preparing a tablet comprising Ceritinib according to any one of items 43 to 51, wherein Ceritinib is used in a dose of at least 150 and up to 750 mg, preferably is at least 150 mg and up to 375 mg, more preferably a Ceritinib dose is 150 mg or 375 mg, particularly is 375 mg.

53. The process for preparing a tablet comprising Ceritinib according to any one of items 43 to 51, wherein Ceritinib is used in a dose of 300 mg.

54. The process for preparing a tablet comprising Ceritinib according to any one of items 43 to 53, wherein the at least one pharmaceutical excipient is magnesium stearate.

55. The process for preparing a tablet comprising Ceritinib according to item 54, wherein at least 0.5 and up to 3 weight percent of magnesium stearate based on the total weight of the uncoated tablet is used, preferably at least 1 and up to 2 weight percent of magnesium stearate, more preferably at least 1.3 and up to 1.7 weight percent of magnesium stearate, particularly 1.5 weight percent of magnesium stearate based on the total weight of the uncoated tablet.

56. The process for preparing a tablet comprising Ceritinib according to any one of items 43 to 55, wherein the tablet comprises at least 40 and up to 70 weight percent of Ceritinib, preferably at least
45 and up to 70 weight percent, more preferably at least 50 and up to 70 weight percent, yet more preferably at least 55 and up to 65 weight percent, particularly 60 weight percent of Ceritinib based on the total weight of the uncoated tablet.

57. The process for preparing a tablet comprising Ceritinib according to any one of items 35 to 46, wherein the tablet has hardness of at least 45 N, preferably at least 50 N, between 50 and 82 N, preferably between 58 and 72 N, most preferably between 64 and 71N, when the tablet contains 150 mg or more and below 300 mg of ceritinib, or has a hardness of at least 100 N, preferably at least 150 N, when the tablet contains 300 mg or more of ceritinib.

58. The pharmaceutical composition according to any one of items 1 to 25, or 39 to 41, or the tablet according to any one of items 26 to 41, for use as a medicine.

59. The pharmaceutical composition according to any one of items 1 to 25, or 39 to 41, or the tablet according to any one of items 26 to 41, for use in the treatment of anaplastic lymphoma kinase (ALK)-positive non-small cell lung cancer (NSCLC).

60. The pharmaceutical composition according to any one of items 1 to 25, or 39 to 41, or the tablet according to any one of items 26 to 41, for use in the treatment according to item 59, wherein the cancer has progressed on or is intolerant to crizotinib.

61. The pharmaceutical composition according to any one of items 1 to 25, or the tablet according to any one of items 26 to 38, wherein the Ceritinib dose is 300 mg.

The terms "a" and "an" and "the" and similar references in the context of describing the disclosure (especially in the context of the following claims) are to be construed to cover both the singular and the plural, unless otherwise indicated herein or clearly contradicted by context. Where the plural form is used for compounds, patients, cancers and the like, this is taken to mean also a single compound, patient, or the like.

The term "comprising" is used herein in its open-ended and non-limiting sense unless otherwise noted. In a more limited embodiment, "comprising" can be replaced by "consisting of", which is no longer open-ended. In a most limited version it can include only features, steps or values as listed in the respective embodiment.

The term "high drug load" denotes more than 40 and up to 70 weight percent of Ceritinib based on the total weight of a composition or a dosage form core, e.g. of an uncoated tablet. In one embodiment, it denotes 50 and up to 70 weight percent of Ceritinib based on the total weight of a composition or a dosage form core, or at least 55 and up to 65 weight percent of Ceritinib based on the total weight of a composition or a dosage form core. In one embodiment the "high drug load" is used to mean about 60 weight percent, specifically 60 weight percent of the drug based on the total weight of a composition or a dosage form core. Similarly, all weight portions disclosed herein are calculated based on the total weight of a composition or a dosage form core, e.g. a non-coated tablet. Any weight gains due to coating are not included in the total weight. Ceritinib mass in a tablet can be for example 150 mg or up to 1000 mg, preferably between 150 mg and 750 mg. Specific Ceritinib doses in high drug load pharmaceutical formulations are respectively and independently from one another 150 mg, 300 mg and 375 mg of ceritinib.

The term "treatment" as used herein comprises a treatment relieving, reducing or alleviating at least one symptom in a subject, increasing progression-free survival, overall survival, extending duration of response or delaying progression of a disease. For example, treatment can be the diminishment of one or several symptoms of a disorder or complete eradication of a disorder, such as cancer. Within the meaning of the present disclosure, the term "treatment" also denotes to arrest, delay the onset (i.e., the period prior to clinical manifestation of a disease) and/or reduce the risk of developing or worsening a disease in a patient, e.g., a mammal, particularly the patient is a human.

The term "therapeutically effective amount" of a therapeutic agent is an amount sufficient to provide an observable improvement over the baseline clinically observable signs and symptoms of the disorder treated with the therapeutic agent, i.e. ceritinib. When the formulation is administered to a patient in need thereof, the therapeutically effective amount will be administered to a patient in need thereof.

DETAILED DESCRIPTION OF THE INVENTION

It was found that a tablet comprising a high-drug load of Ceritinib with sufficient tablet hardness and without sticking/picking during the manufacturing can only be manufactured by wet granulation. Direct compression and roller compaction did not yield satisfactory results. The problem was encountered that by using direct compression and roller compaction, and to a lesser extent a "standard" wet granulation formulation, where substantially all excipients are blended together with a pharmaceutically active ingredient and together wet granulated, the physical properties of the final blend showed a very narrow compressibility window and led to tablets with very poor cohesion properties, bad friability results and still sticking and capping on both surfaces. On the other hand, wet granulation of Ceritinib only with a binder was easy to process and provided pharmaceutical composition with significantly improved compressibility and no sticking and resulted in tablets with reduced friability. A pharmaceutical composition comprising more than 40 and up to 70 weight percent of Ceritinib based on the total weight of the pharmaceutical composition, or weight percent of Ceritinib based on the total weight of the pharmaceutical composition was easily obtained. Other drug loads, such as at least 45 and up to 70, 50 and up to 70, at least 55 and up to 65, or particularly 60 weight percent of Ceritinib based on the total weight of the pharmaceutical composition, can also be prepared. When calculating the Ceritinib content based on the total weight of a pharmaceutical composition, which is a capsule, weight of the capsule shell is included in the total weight of the pharmaceutical composition. In case where the pharmaceutical composition is a coated tablet, only the tablet core should be taken into account, i.e. the total weight of the pharmaceutical composition is the uncoated tablet.

Specifically, ceritinib drug substance can be wet granulated using one pharmaceutically acceptable excipient, a binder, which can be added to the drug substance in a dissolved state (e.g. in an aqueous solution) or in a powder form and then granulated by adding a granulation liquid. A combination of more than one binder can be used. The wet granulation can be performed using a standard high shear granulator to form drug wet granules. The solvents used for wet granulation can be for example water, or low alkyl alcohols like ethanol, propanol, isopropanol, ethers, or mixtures thereof. The wet granules comprising Ceritinib and the binder are subsequently dried. The material can be dried by using for example a fluid bed drier. Removing substantially all granulation liquid can be advantageous in terms of reducing unnecessary stickiness of the granulation mass due to the remaining granulation liquid. The obtained granules can be also calibrated, which can be achieved by a sieving method or the like, for example by using an oscillating sieve.

The binder used for wet granulation of the active ingredient can be a polymer that is otherwise suitable pharmaceutically acceptable binder or a coating polymer. Particularly suitable binders are for example starches, such as for example potato, wheat or corn starch, Hypromellose (named also Hydroxypropylmethyl cellulose), Hydroxypropyl cellulose, Hydroxy ethyl cellulose, Povidone (named also Polyvinylpyrrolidone), Copovidone (also named copolyvidone), Gelatine and Polymethacrylates. By using the wet granulation process for granulating Ceritinib with mainly the binder, the compressibility and stickiness are immensely improved. In one embodiment the binder is povidone. By specifically selecting Povidone as a binder the friability of the final tablet can be further improved.

The overall characteristics of the pharmaceutical composition are further enhanced, if the drug-binder granules form an inner phase, and additional pharmaceutically acceptable excipients are added to the blend as an outer phase. This way, the stickiness of the composition can be further reduced. The composition can contain further pharmaceutical excipients, which can be in the outer phase, or elsewhere, and can be pharmaceutically acceptable excipients such as filler, disintegrant, glidant, and/or lubricant, or mixture thereof. Further excipients like antioxidants, sweetening agents, flavoring agents, dyes, and the like and combinations thereof can also be added. The composition can comprise one or more fillers, for example a microcrystalline cellulose, silicified microcrystalline cellulose, lactose (anhydrous, monohydrate), starch, mannitol, sorbitol, calcium phosphate (dibasic anhydrous, dibasic hydrate, tribasic), isomalt, sucrose, Hydroxypropyl Cellulose Low-substituted; one or more disintegrants, for example Croscarmellose Sodium, Crospovidone, Sodium starch glycolate, microcristalline cellulose, silicified microcrystalline cellulose, Hydroxypropyl Cellulose Low-substituted, cellulose powdered; further binders, such as for example starch, Hydroxypropyl Cellulose Low-substituted, Hypromellose (Hydroxypropylmethyl cellulose), Hydroxypropyl cellulose, Hydroxy ethyl cellulose, Povidone (Polyvinylpyrrolidone), Copovidone (Copolyvidone), gelatine, polymethacrylates; one or more glidants, for example Silica, colloidal silica, talc, hydrophobic colloidal silica, magnesium silicate; or one or more lubricants, for example Magnesium stearate, calcium stearate, zinc stearate, glyceryl mono fatty acid, glyceryl monostearate, glyceryl dibehenate, glyceyryl palmito stearic ester, or polyoxyethylen glycol; or mixtures thereof. They can be added in a powder form, as separately granulated granules, or dissolved in a fluid, which can then be substantially removed by drying throughout the process, or added after going through the process of briquetting or slugging, and optionally sieving. Excipient "in a dry powder form" or "dry excipient" mean herein that an excipient is substantially free of water or moisture, preferably the excipient is dry. Using only dry excipients in the outer phase normally does not worsen the sticking and picking problem and can even improve it.

Some excipients can act as a binder, filler and/or a disintegrant, depending on their content in the blend, coexisting excipients and how and when they are formulated in the formulation. It is completely in the purview of a pharmaceutical technologist to understand the role of a pharmaceutical excipient in the composition. He will be able to assess the role of the excipient in the pharmaceutical composition or the dosage form based on the characteristics he wants to achieve, such as volume, hardness, dissolution profile etc, of a pharmaceutical composition or a dosage form. The outer phase comprising one or more pharmaceutically acceptable excipients is mixed with the inner phase (granulate) using e.g. a free fall mixer. In one embodiment, the outer phase comprises Cellulose Microcristalline as filler, Hydroxypropyl Cellulose Low-substituted as dry binder and Croscarmellose Sodium as disintegrant. The formulation may also contain one glidant, most preferably colloidal silicon dioxide.

Adding Hydroxypropyl cellulose low substituted in the outer phase further helps reduce friability of the tablets obtained from the pharmaceutical composition. The content of Hydroxypropyl cellulose low substituted in the outer phase can be around 5 wt % based on the on the total weight of the pharmaceutical composition. Hydroxypropyl cellulose low substituted differs from Hydroxypropylmethyl cellulose (HPMC, hypromellose) or even plain Hydroxypropyl cellulose (HPC). The latter two polymers are water soluble and can be used as binders for granulation, in which case they normally get dissolved in the granulation liquid. In alternative, they are simply added to the mass in powder form and dissolve and intertwine the granulation mixture during granulation process. On the other hand, Hydroxypropyl cellulose low substituted is much less water soluble. Friability can be measured by a friability test as described in the 8$^{th}$ Edition of European Pharmacopoeia (version 8.1) by using the tablet friability apparatus. The friability of uncoated tablet cores is measured, as coated tablets normally do not show any friability. Generally, the method measures weight loss of tablets after mechanical stress has been applied to them. A drum of predefined measurements is rotated 100 times with 10 tablets (depending on the tablet mass) that have been carefully dedusted and accurately weighted before the testing. After rotations, the tablets are cleaned of any loose dust and again weighted. Maximum loss of mass not greater than 1% is considered acceptable. The prescribed test for friability of uncoated tablets of Eu. Ph. Ed. 8 (8.1) defines additional specifics.

To the pharmaceutical composition, a lubricant, preferably magnesium stearate, can be added to further counter the sticking of the blend. The amount of the lubricant in the pharmaceutical composition can be at least 0.5 and up to 3 weight percent, preferably at least 1 and up to 2 weight percent, particularly 1.5 weight percent based on the total weight of the pharmaceutical composition. The lubricant is preferably magnesium stearate. In one alternative, instead of increasing the amount of the lubricant to the pharmaceutical composition, it can be sprayed and deposited on the material contacting surfaces of pressing tools, e.g. punches and/or dies of the tableting machine before compression. The amount of lubricant impacts the compressibility, hardness, friability and dissolution profile of the final dosage form, i.e. tablet. Higher is the amount of a lubricant, lower are the compressibility and hardness, but friability increases. The lubricant reduces sticking of the blend, but does not influence the dissolution to the extent that would change the bioequivalence remains the same.

The pharmaceutical composition is then processed to prepare a final dosage form—a tablet. This can be achieved by compressing the final blend for example on a rotary tablet press. Tablet of different shapes can be prepared (round, ovaloid, or other suitable shape). The pharmaceutical formulation or the tablet can have further layers and coatings. One possible coating can be for example a colour coating. The shape, the final mass and the drug load dictate the dosage strength of the tablet. The tablet can contain for example a 150 mg dose of ceritinib. Given the high drug load, the tablet of the present disclosure can contain at least 150 and up to 750 mg, preferably is at least 300 mg and up to 375 mg. The tablet can have 300 mg Ceritinib. In one specific embodiment, which is preferred, the Ceritinib dose in the tablet is 375 mg. Increasing the dose in a single unit dosage form reduces the daily pill burden compared to the approved capsule formulation dosing regimen.

In one embodiment, the tablet of 150 mg strength has a hardness of at least 45 N, but preferably has at least 50 N. Tablets exhibiting hardness of between 50 and 82 N, preferably between 58 and 72 N, most preferably between 64 and 71N, measured by tablet hardness tester as described in European Pharmacopeia Ed. 8 (version 8.1 in chapter 2.9.8 titled Resistance to crushing of tablets. In summary, tablets are placed between the jaws of the apparatus. The jaws move towards each other and crush the tablet. The apparatus records the force needed to crush the tablet with a precision of 1 Newton (1 N). For tablets comprising more than 300 mg Ceritinib, e.g. 300 mg or 375 mg, hardness of 100 N or more is desired, preferably hardness of 150 N or more. Tablet hardness does not grow indefinitely, but normally increases to a certain plateau, and does not increase anymore with increased compression force. The hardness and the content of the lubricant, e.g. magnesium stearate is linked to the dissolution profile. The composition of the present disclosure can achieve comparable dissolution profile of the FDA approved capsules. Therefore, it is expected that the present composition may achieve at least the same therapeutic effect as currently approved Ceritinib capsules.

The tablet comprising Ceritinib can be prepared by wet granulation. Particularly the process of preparing the tablet comprises the steps of: a) Preparing granules comprising Ceritinib and a binder by wet granulation, b) mixing the granules with at least one other pharmaceutical excipient to obtain a mixture, and c) compressing the mixture in the tablet. However, all excipients can be wet granulated with the active and compressed in the tablet. The steps a), b) and c) of the process can be employed as described above. Mixing in step b) can be carried out in the absence of any granulation liquid, so that the blend obtained is substantially dry. This can help reduce the sticking and picking problem of Ceritinib. The process can further comprise the steps of calibrating the granule size, depositing a lubricant on the surfaces of a pressing tool, particularly tableting machine punches, and/or coating a tablet. Calibrating the granule size can be achieved by sieving. Extra fine particles and bulky granules can be removed to improve flowability of the granules in bulk. Coating can be film coating and can be obtained by spraying the solution or a suspension of a coating polymer on the tablet cores. Optionally the coating solution or suspension comprises further excipients such as a colorant or plasticizer. The coating can take place for example in a coating drum or a wurster apparatus.

The process is suited to prepare tablets comprising at least 150 and up to 750 mg Ceritinib. Preferably the dose of Ceritinib is at least 150 mg and up to 375 mg, including 300 mg. In one embodiment, the Ceritinib dose is 150 mg. In another preferred embodiment, the dose is 375 mg. In another embodiment, the dose is 300 mg. Magnesium stearate improves the processability and can be added to the pharmaceutical mixture for tableting in at least 0.5 and up to 3 weight percent based on the total weight of the mixture, at least 1 and up to 2 weight percent, preferably at least 1.3 and up to 1.7 weight percent, particularly 1.5 weight percent of magnesium stearate based on the total weight of the mixture. The process is suitable to yield tablets with high drug load. Tablets with even 70 weight percent of active ingredient can be prepared. Also other percent ranges of the active can be easily obtained, for example the tablet with at least 40 and up to 70 weight percent of Ceritinib, preferably at least 45 or 50 and up to 70 weight percent, more preferably at least 55 and up to 65 weight percent, particularly 60 weight percent of Ceritinib based on the total weight of the uncoated tablet. When appropriate amount of a lubricant, e.g. magnesium stearate, is added, the process leads to a tablet with hardness of at least 45 N for a tablet comprising at least 150 mg Ceritinib and less than 300 mg. The hardness of said tablet can be between 50 and 82 N, preferably between 58 and 72 N, most preferably is between 64 and 71N. Tablets with larger dose, e.g. with doses of 300 mg or more, e.g. up to 750 mg, particularly 375 mg, should have harness of 100 N or more, preferably of 150 N or more.

The pharmaceutical composition or the tablet according to the present disclosure can be used as a medicine. Ceritinib is primarily indicated for the treatment of patients with a proliferative disease. The proliferative disease according to the present disclosure can be cancer. The cancer includes lung cancer. In one embodiment the proliferative disease is a non-small cell lung cancer, particularly is. The descriptor ALK-positive refers to anaplastic lymphoma kinase (ALK) being mutated in a way that leads to activation or higher activity of ALK compared to the activity of the wild type ALK or ALK in a healthy control. The pharmaceutical composition or the tablet can be used to treat ALK-positive non-small cell lung cancer, wherein the cancer has progressed on or is intolerant to crizotinib. In the same manner the pharmaceutical composition or the tablet can be used for the manufacture of the medicament, particularly for the treatment of the aforementioned diseases. Equally, the method of treating a patient in need of ceritinib, the method comprising administering the pharmaceutical composition or the tablet according of the present disclosure is also contemplated herein.

EXAMPLES

The following Examples illustrate the disclosure described above; they are not, however, intended to limit the scope of the disclosure in any way. The beneficial effects of the ceritinib for use in the treatment according to the present disclosure, or methods as disclosed herein can also be determined by other test models known as such to the person skilled in the pertinent art.

All experiments described hereinafter were performed by using the following laboratory or manufacturing equipment:
Granulator: Top or bottom driven High shear mixer.
Sieve: Manual hand sieve, oscillating and rotating sieve mill
Drying: Fluidized bed dryers
Tableting machine: Compaction simulator/Excentric tableting machine, rotary tableting machine
Roller compactor: Cantilevered roll design and feature a vertical tapered deed screw system
Film coating drum: Perforated drum coater
Dissolution apparatus: USP II Dissolution apparatus Examples 1 to 3A: Appropriate Formulation Technology It was determined during the formulation preworks that all formulations tested showed very significant sticking issues during a tableting step. The sticking issue was occurring at all three tested common manufacturing processes for tablets, either direct blending/compression, roller compaction/compression or wet granulation/compression. However, the sticking issue was significantly reduced using wet granulation. In addition, the wet granulation approach allowed loading of the highest amount of drug. Roller compaction and direct compression did not result in an appropriate tablet or an acceptable manufacturing process, leading to the conclusion to that these technologies could not be selected. For direct compression (example 1) all listed excipients except magnesium stearate were blended, then Mg-stearate was added and the mix blended again and compressed.

Roller compaction approach (dry granulation) shown in example 2 was done by blending LDK378 drug substance, Mannitol, and a portion of Cellulose microcrystalline, Crospovidone, Colloidal silica and Mg-stearate as an inner phase and dry compacting it, while another portion of Cellulose microcrystalline, Crospovidone, Colloidal silicon dioxide and Mg-stearate was added as the extra-granular phase, mixed with the granules and compressed.

Wet granulation (example 3) was done by using LDK378 drug substance, Mannitol, Hypromellose and a portion of Cellulose microcrystalline and Croscarmellose Sodium as an inner phase, while using the rest of Cellulose microcrystalline, Croscarmellose-Sodium together with Colloidal silicon dioxide and Mg-stearate as an extra granular phase.

TABLE 1

| | LDK378 tablets-150 mg dose | | |
|---|---|---|---|
| Ingredient (Pharm.Eur.) | Example 1 (Direct compression) Quantity [%] per tablet | Example 2 (Roller compaction) Quantity [%] per tablet | Example 3A (Wet granulation) Quantity [%] per tablet |
| LDK378 drug substance | 40.0 | 40.0 | 60.0 |
| Cellulose, Microcrystalline | 40.0 | 40.0 | 13.0 |
| Mannitol | — | 10.0 | 15.0 |
| Hypromellose | — | — | 4.0 |
| Hydroxypropyl Cellulose, Low-substituted | 9.5 | — | — |
| Sodium Starch Glycolate | 8.0 | — | — |
| Croscarmellose Sodium | — | — | 6.0 |
| Crospovidone | — | 8.0 | — |

TABLE 1-continued

LDK378 tablets-150 mg dose

| Ingredient (Pharm.Eur.) | Example 1 (Direct compression) Quantity [%] per tablet | Example 2 (Roller compaction) Quantity [%] per tablet | Example 3A (Wet granulation) Quantity [%] per tablet |
|---|---|---|---|
| Colloidal Silicon Dioxide | 1.0 | 0.5 | 0.5 |
| Magnesium Stearate | 1.5 | 1.5 | 1.5 |
| Water (for granulation) | — | — | qs |
| Tablet shape/dimension | | Round, 11 mm diameter | Round, 9 mm diameter |
| Tablet weight [mg] | | 375 | 250 |
| Observation | Not possible to compress | Very strong picking and sticking | Slight tendency to picking and sticking |

It was concluded that the tablet comprising at least 40 wt % of ceritinib can only be prepared by wet granulation followed by compression.

Examples 3B to 6: Appropriate Binder

In an additional development step, the impact of the choice of a binder for a wet granulation phase was determined. Hypromellose and povidone were selected for testing out of several binder types (starch based binders, povidone based binders, copovidone based binders, hypromellose based binders, hydroxypropylcellulose based binders and hydroxyethylcellulose based binders) (cf. examples 4 and 5 in table 2). A binder for wet granulation can be added either in a dry state to the granulation mixture (granule phase) before the wet granulation is conducted with water or the binder can be dissolved in e.g. water to form a granulation liquid, which is then used to conduct the wet granulation of the granulation mixture. The granulation mixture can consist of a drug substance and several excipients (e.g. filler, disintegrant and/or other excipients) which are granulated together with the applied binder (examples 4 and 5). However, a specifically modified approach was taken, by which only the drug and the binder got wet granulated and represent an inner phase, whereas the remainder of pharmaceutical excipients was added afterwards as an outer phase (example 6). In this novel granulation process, only drug substance (without any additional excipients) was granulated using dissolved povidone as the binder. The obtained drug substance granules were blended with the outer phase and compressed into tablets.

TABLE 2

LDK378 tablets-150 mg dose
150 mg dose tablets

| Ingredient (Pharm.Eur.) | Example 3B (standard WG, hypromellose added dry) Quantity [%] per tablet | Example 4-wet granulation (binder hypromellose, added dissolved) Quantity [%] per tablet | Example 5-wet granulation (binder povidone, added dissolved) Quantity [%] per tablet | Example 6-wet granulation (binder povidone, added dissolved, added only to drug substance) Quantity [%] per tablet |
|---|---|---|---|---|
| LDK378 | 70.0 | 60.0 | 60.0 | 60.0 |
| Povidone | — | — | 4.0 | 4.0 |
| Hypromellose | 4.0 | 4.0 | — | — |
| Cellulose, Microcrystalline | 13.0 | 13.0 | 13.0 | 13.0 |
| Mannitol | 5.0 | 15.0 | 15.0 | 15.0 |
| Croscarmellose Sodium | 6.0 | 6.0 | 6.0 | 6.0 |
| Colloidal Silicon Dioxide | 0.5 | 0.5 | 0.5 | 0.5 |
| Magnesium Stearate | 1.5 | 1.5 | 1.5 | 1.5 |
| Water (for granulation) | qs | qs | qs | qs |
| Tablet shape/dimension | Round, 9 mm diameter | Round, 9 mm diameter | Round, 9 mm diameter | Round, 9 mm diameter |
| Tablet weight [mg] | 250 | 250 | 250 | 250 |
| Tablet hardness | <45N (at 29kN force) | <50N (at 25kN force) | approx. 50N (at 25kN force) | approx. 70N (at 20kN force) |
| Tablet friability | 1.3% | 1.2% | 0.9% | 0.5% |
| Observation | Insufficient compressibility, no sticking | Insufficient compressibility, no sticking | Still insufficient compressibility, no sticking, friability improved | Significant improved compressibility, no sticking, friability improved |

The choice of the binder type did not significantly improve the compressibility. However, povidone did improve the friability. A significant improvement of the compressibility was achieved by direct granulation of the LDK378 drug substance with dissolved povidone. After drying of the wet granules, all other excipients were added as the outer phase and compressed into tablets. The tablet hardness during compression significantly improved, although a similar or lower compression force was used, which was an unexpected improvement. This good compressibility of LDK378 film-coated tablets was achieved by using the novel granulation technique, whereby solely drug substance and povidone as the binder were granulated. The tablets disintegrated within 15 minutes, which meet the requirement for immediate release tablets.

Figure 1:
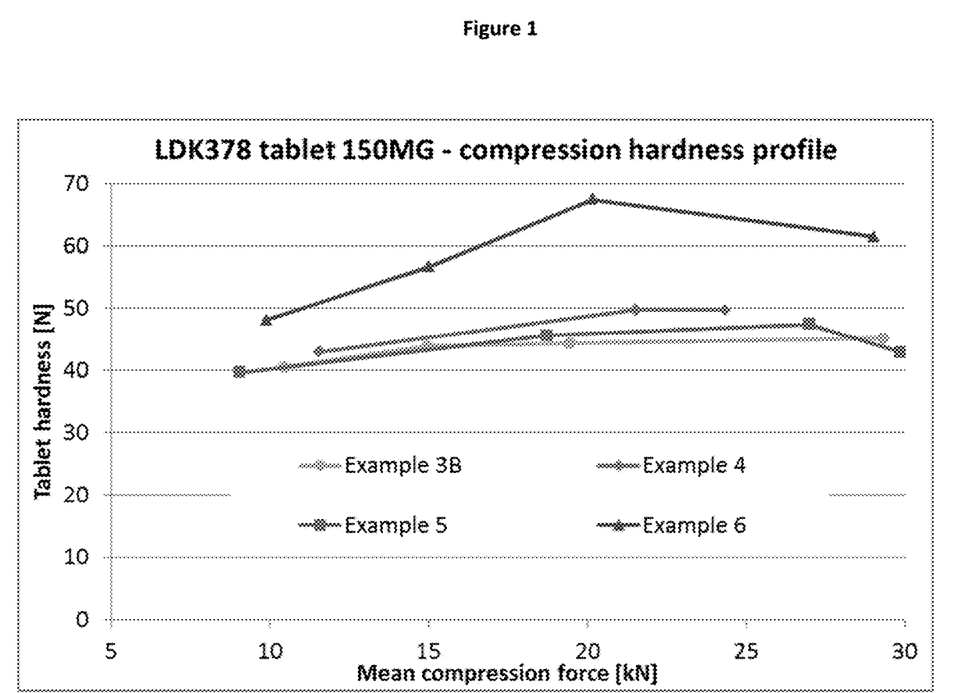
FIG. 1 The figure show the tablet hardness versus the applied compression force of compositions described in examples 3B to 6.
Figure 2:
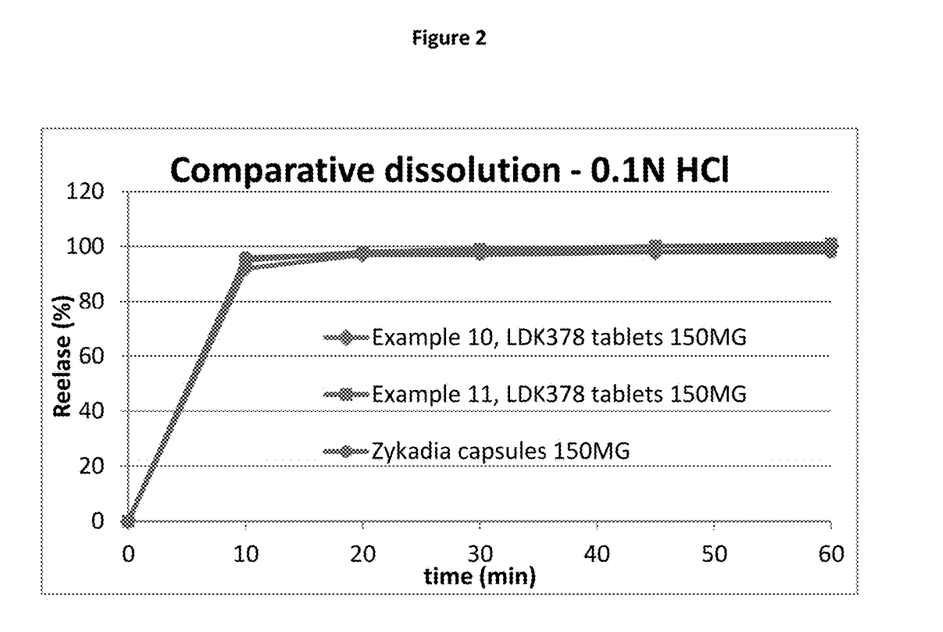
FIG. 2 Dissolution profile (pH 1) of a tablet described in Examples 10 and 11 versus capsule (Zykadia®) formulation.
Figure 3:
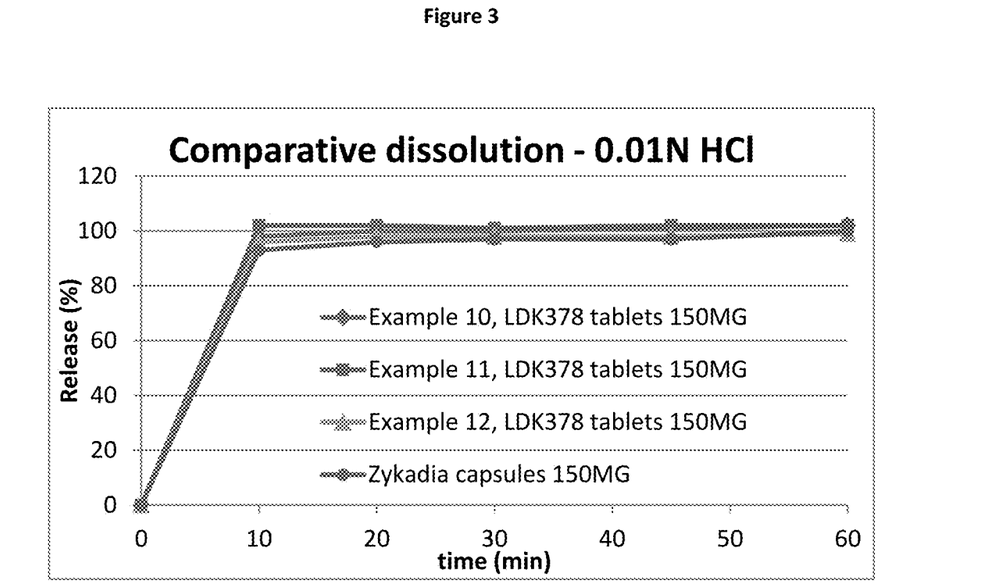
FIG. 3 Dissolution profile (pH 2) of a tablet described in Examples 10, 11 and 12 versus capsule (Zykadia®) formulation.
Figure 4:
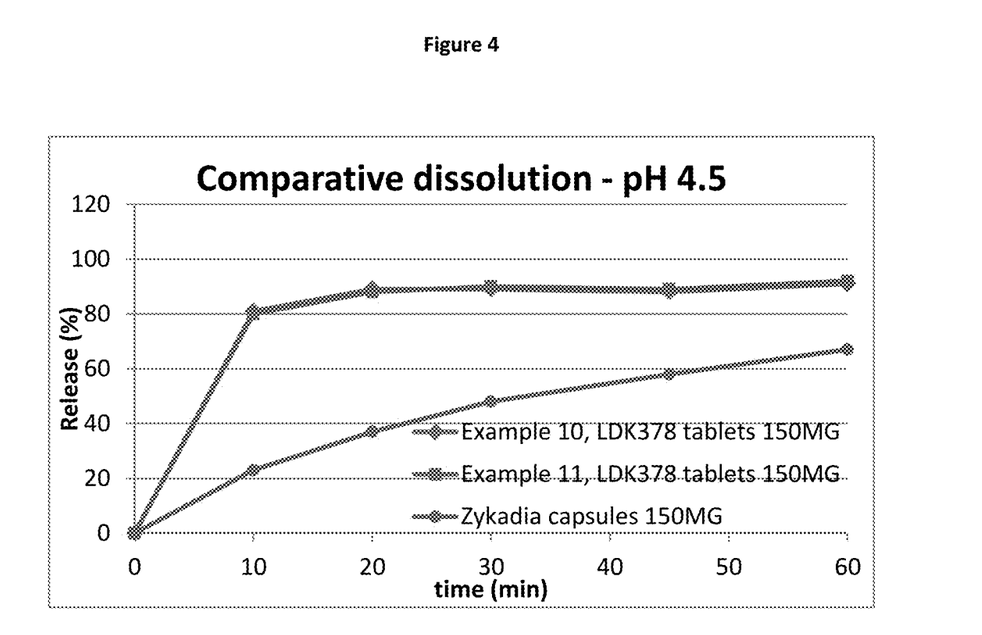
FIG. 4 Dissolution profile (pH 4.5) of a tablet described in Examples 10 and 11 versus capsule (Zykadia®) formulation.
Figure 5:
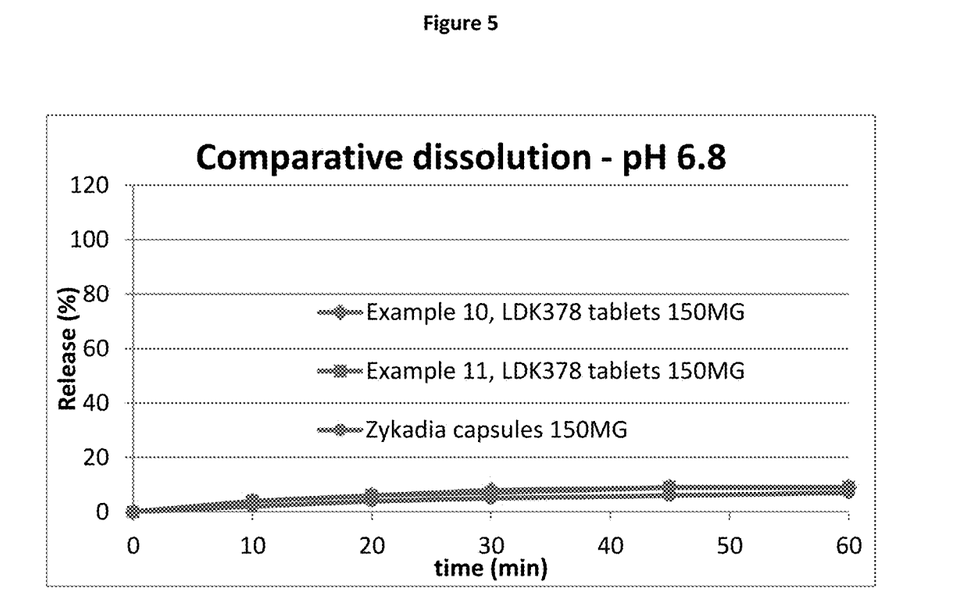
FIG. 5 Dissolution profile (pH 6.8) of a tablet described in Examples 10 and 11 versus capsule (Zykadia®) formulation.

In addition, the superior compressibility was demonstrated, which can be observed by plotting the tablet hardness versus the applied compression force (FIG. 1).

Examples 7 to 9: Excipients for an Improved Outer Phase

The tablets were prepared by the specific wet granulation process comparable to Example 6. Soluble filler mannitol in the outer phase was replaced by higher amount of microcrystalline cellulose and an additional dry binder was added to the outer phase. Two different dry binders, Hydroxypropyl Cellulose Low-substituted and Copovidone were evaluated at 5% level in the outer phase (see example 8 and 9). The friability went from 0.65% to 0.11% when using Hydroxypropyl Cellulose Low-substituted. Overall, these formulation development activities led to reduced tablet friability and further increase compressibility.

TABLE 3

LDK378 tablets-150 mg dose; WG—wet granulation

| Ingredient (Pharm.Eur.) | Example 7 (WG-60% DL, novel granulation) Quantity [%] per tablet | Example 8 (WG-60% DL, novel granulation) Quantity [%] per tablet | Example 9 (WG-60% DL, novel granulation) Quantity [%] per tablet |
|---|---|---|---|
| LDK378* | 60.0 | 60.0 | 60.0 |
| Povidone* | 4.0 | 4.0 | 4.0 |
| Cellulose, Microcrystalline | 20.0 | 25.0 | 25.0 |
| Mannitol | 10.0 | — | — |
| Croscarmellose Sodium | 4.0 | 4.0 | 4.0 |
| Copovidone | — | — | 5.0 |
| Hydroxypropyl Cellulose Low-substituted | — | 5.0 | — |
| Colloidal Silicon Dioxide | 0.5 | 0.5 | 0.5 |
| Magnesium Stearate | 1.5 | 1.5 | 1.5 |
| Water (for granulation) | qs | qs | qs |
| Tablet shape/dimension | Round, 9 mm diameter | Round, 9 mm diameter | Round, 9 mm diameter |
| Tablet weight [mg] | 250 | 250 | 250 |
| Tablet hardness | approx. 75N (at 21kN force) | approx. 78N (at 17kN force) | approx. 82N (at 17kN force) |
| Friability | 0.7% | 0.1% | 0.5% |
| Conclusion | Sufficient compressibility, no sticking | Sufficient compressibility, no sticking, minimized friability | Sufficient compressibility, no sticking, reduced friability |

*LDK378 (Ceritinib) and povidone were granulated alone, and subsequently mixed with the remaining excipients (outer phase).

Examples 10 to 12: Lubricant Content

The tablets were prepared by the specific wet granulation process comparable to Example 6, with only Ceritinib (LDK378) and the binder being granulated and making the inner phase. The sticky nature of LDK378 drug substance was observed. Trials on direct compression and roller compaction (see example 1 and 2) failed due to strong sticking during manufacturing. Solely by implementing wet granulation technology, the sticking tendency was reduced to a minimum (see examples 3A and 3B). The implementation of the novel granulation technology, whereby drug substance is directly granulated with a binder to form the inner phase of granules, further reduced observed stickiness to a minimum. Nevertheless, the amount of lubricant can further reduce the stickiness during compression.

TABLE 4

LDK378 tablets-150 mg

| Ingredient (Pharm.Eur.) | Example 10 (WG-60% DL, 1.0% lubricant) Quantity [%] per tablet | | Example 11 (WG-60% DL, 1.3% lubricant) Quantity [%] per tablet | | Example 12 (WG-60% DL, 1.5% lubricant) Quantity [%] per tablet | |
|---|---|---|---|---|---|---|
| LDK378 drug substance | 60.0 | | 60.0 | | 60.0 | |
| Povidone | 4.0 | | 3.0 | | 4.0 | |
| Cellulose, Microcrystalline | 23.5 | | 24.2 | | 23.0 | |
| Croscarmellose Sodium | 6.0 | | 5.0 | | 6.0 | |
| Hydroxypropyl Cellulose Low-substituted | 5.0 | | 6.0 | | 5.0 | |
| Colloidal Silicon Dioxide | 0.5 | | 0.5 | | 0.5 | |
| Magnesium Stearate | 1.0 | | 1.3 | | 1.5 | |
| Water (for granulation) | qs | | qs | | qs | |
| Tablet shape/dimension | Round, 9 mm diameter | | Round, 9 mm diameter | | Round, 9 mm diameter | |
| Tablet weight [mg] | 250 | | 250 | | 250 | |
| Tablet hardness | 70N (18kN force) | 69N (21kN force) | 64N (20kN force) | 67N (22kN force) | 58N (21kN force) | 72N (26kN force) |
| Friability | 0.1% | 0% | 0.2% | 0.2% | 0.3% | 0.2% |
| Sticking (rated 0-5*) | 4 | 3 | 3 | 0 | 0 | 0 |
| Conclusion | Sticking occurred | | Minimized sticking | | No sticking | |

*Explanation: 0 = no sticking, 5 = strong sticking
WG—wet granulation,
DL—drug load Examples 10-12 demonstrate the need for adequate lubrication of the composition. Above lubrication levels of 1.3%, the sticking is reduced to a minimum and at 1.5% no sticking was observed. However, examples 10-12 also demonstrate the impact of high lubrication on the compressibility and friability, whereby both, the compressibility as well as the friability can be negatively impacted by higher amounts of a lubricant. As shown in example 12, a stable manufacturing process was achieved by the novel granulation technology together with the adapted outer phase and the optimized lubricant concentration, leading to a formulation and process resulting in a tablet with suitable compressibility and friability, while no sticking occurs during manufacturing.

In addition, comparative dissolution profiles of formulations from examples 10, 11 and 12 demonstrate that the lubricant content does not significantly affect the dissolution (cf. FIGS. 2 to 5). Based on these results it can be expected that film coated tablets and capsules of LDK378 show similar results in-vivo during bridging or bioequivalence studies.

Examples 13 to 18: Non-Limiting Examples and Dissolution Profiles

The manufacturing process for LDK378 150 mg tablet (optionally film-coated) is as follows:

Granulation:
1. Fill LDK378 drug substance into the high shear granulator and mix.
2. Dissolve povidone in water to prepare the granulation liquid.
3. Add povidone solution from step 2 to the granulator for wetting and kneading to prepare the granules.
4. Dry the obtained granules from step 3 in a fluid bed dryer.
5. Sieve the dried granules from step 4. In one variant, the sieve can have mesh with openings of 0.8 mm.

Final Blend:
6. Sieve and add microcrystalline cellulose, low-substituted hydroxypropyl cellulose, croscarmellose sodium and colloidal silicon dioxide to the granules from step 5.
7. Blend the mixture from step 6.
8. Add sieved magnesium stearate to the blend from step 7.
9. Blend the mixture from step 8 to obtain the final blend.

Compression:
10. Compress the final blend from step 9 to tablet cores.

Optionally Coating:
11. Suspend the coating premixes (e.g. HPMC and non-functional color coating) in water to prepare the coating suspension.
12. Film-coat the compressed tablets from step 10 with the coating suspension from step 11.

Following compositions (example 13 to example 18) are non-limitative and illustrate the invention, including all strength of LDK378, which is 150 mg, 300 mg and 375 mg. Especially the 375 mg strength demonstrate the benefit of the current formulation for patient, since the pill burden is reduced from 5 capsules of 23.3 mm size (capsule size 00) to 2 tablets of 17 mm size per day.

TABLE 5

| Ingredient (Pharm.Eur.) | Example 13 (WG-60% DL, 150 MG strength) Quantity [%] per tablet | Example 14 (WG-60% DL, 300 MG strength) Quantity [%] per tablet | Example 15 (WG-60% DL, 375 MG strength) Quantity [%] per tablet |
|---|---|---|---|
| LDK378 drug substance | 60.0 | 60.0 | 60.0 |
| Povidone | 4.0 | 4.0 | 4.0 |

TABLE 5-continued

|  | Example 13 (WG-60% DL, 150 MG strength) Quantity [%] per tablet | Example 14 (WG-60% DL, 300 MG strength) Quantity [%] per tablet | | Example 15 (WG-60% DL, 375 MG strength) Quantity [%] per tablet | |
| --- | --- | --- | --- | --- | --- |
| Ingredient (Pharm.Eur.) | | | | | |
| Cellulose, Microcrystalline | 25.0 | 25.0 | | 25.0 | |
| Croscarmellose Sodium | 4.0 | 4.0 | | 4.0 | |
| Hydroxypropyl Cellulose Low-substituted | 5.0 | 5.0 | | 5.0 | |
| Colloidal Silicon Dioxide | 0.5 | 0.5 | | 0.5 | |
| Magnesium Stearate | 1.5 | 1.5 | | 1.5 | |
| Water (for granulation) | qs | qs | | qs | |
| Tablet shape/dimension | Round, 9 mm diameter | Ovaloid, 16 × 6.3 mm | | Ovaloid, 17 × 6.7 mm | |
| Tablet weight [mg] | 250 | 500 | | 625 | |
| Tablet hardness | 70N (22kN force) | 147N (13kN force) | 170N (35kN force) | 172N (15kN force) | 199N (35kN force) |
| Friability | 0.4% | 0.5% | 0.5% | 0.7% | 1.2% |
| Conclusion | Acceptable compressibility and friability | Acceptable compressibility and friability | | Acceptable compressibility, Friability at upper limit | |

WG—wet granulation,
DL—drug load

TABLE 6

|  | Example 16 150 MG film coated tablet | | Example 17 300 MG film coated tablet | | Example 18 375 MG film coated tablet | |
| --- | --- | --- | --- | --- | --- | --- |
| Ingredients | Quantity [mg] per FCT | Quantity [%] per FCT | Quantity [mg] per FCT | Quantity [%] per FCT | Quantity [mg] per FCT | Quantity [%] per FCT |
| LDK378 drug substance | 150.0 | 57.7 | 300.0 | 58.1 | 375.0 | 58.2 |
| Povidone | 10.0 | 3.8 | 20.0 | 3.9 | 25.0 | 3.9 |
| Purified Water | qs | — | qs | — | qs | — |
| Inner Phase (granulate) | 160.0 | 61.5 | 320.0 | 62.0 | 400.0 | 62.1 |
| Cellulose, Microcrystalline | 62.5 | 24.0 | 125.0 | 24.2 | 156.25 | 24.3 |
| Croscarmellose Sodium | 10.0 | 3.8 | 20.0 | 3.9 | 25.0 | 3.9 |
| Hydroxypropyl Cellulose Low-substituted | 12.5 | 4.8 | 25.0 | 4.8 | 31.25 | 4.9 |
| Colloidal Silicon Dioxide | 1.25 | 0.5 | 2.5 | 0.5 | 3.12 | 0.5 |
| Magnesium Stearate | 3.75 | 1.4 | 7.5 | 1.5 | 9.38 | 1.5 |
| Total core tablet | 250.0 | 96.2 | 500.0 | 96.8 | 625.0 | 97.0 |
| Coating premix* | 10.0 | 3.8 | 16.5 | 3.2 | 19.0 | 3.0 |
| Total film coated tablet | 260.0 | 100.0 | 516.5 | 100.0 | 644.0 | 100.0 |
| Tablet shape/dimension | Round, 9 mm diameter | | Ovaloid, 16 × 6.3 mm | | Ovaloid, 17 × 6.7 mm | |

Coating premix is a basic excipient mix for non-functional film coating containing hypromellose (as film coating polymer), macrogol (plasticizer), talc (anti-tacking agent) and pigments (e.g. iron oxides or titanium dioxide).

The invention claimed is:

1. A pharmaceutical tablet comprising 150 mg to 750 mg of ceritinib and at least one pharmaceutical excipient, wherein the ceritinib is more than 40 and up to 70 percent weight of the tablet, and wherein the ceritinib is present in granules consisting of ceritinib and polyvinylpyrrolidone, and the granules are obtained by wet granulation.

2. The pharmaceutical tablet according to claim 1, further comprising a lubricant.

3. The pharmaceutical tablet according to claim 2, wherein the lubricant is magnesium stearate.

4. The pharmaceutical tablet according to claim 3 comprising at least 0.5 and up to 3 weight percent of magnesium stearate.

* * * * *